United States Patent [19]

Muether et al.

[11] 4,426,716
[45] Jan. 17, 1984

[54] DENTAL X-RAY DIAGNOSTIC INSTALLATION

[75] Inventors: Manfred Muether; Ernest-August Behne, both of Bensheim, Fed. Rep. of Germany

[73] Assignee: Siemens Aktiengesellschaft, Berlin & Munich, Fed. Rep. of Germany

[21] Appl. No.: 211,404

[22] Filed: Nov. 28, 1980

[30] Foreign Application Priority Data

Dec. 6, 1979 [DE] Fed. Rep. of Germany ....... 2949199

[51] Int. Cl.³ .............................................. G03B 41/16
[52] U.S. Cl. ....................................... 378/38; 378/197
[58] Field of Search ................ 378/38, 205, 170, 197, 378/198, 193, 194, 195, 196

[56] References Cited

U.S. PATENT DOCUMENTS

| | | |
|---|---|---|
| 2,946,892 | 7/1980 | Bas-Taymaz . |
| 3,644,735 | 2/1972 | Vandervelden ...................... 378/205 |
| 3,655,967 | 4/1972 | Finkenzeller ......................... 378/196 |
| 4,104,531 | 8/1978 | Weiss ..................................... 378/38 |

FOREIGN PATENT DOCUMENTS 7820937 12/1979 Fed. Rep. of Germany .

OTHER PUBLICATIONS

Siemens Brochure, "Panoramic Radiography with the New Status X2", Siemens Aktiengesellschaft, West Germany.

*Primary Examiner*—Craig E. Church
*Attorney, Agent, or Firm*—Hill, Van Santen, Steadman & Simpson

[57] ABSTRACT

A dental x-ray diagnostic installation comprises x-ray apparatus containing x-ray generator and x-ray tube having a hollow anode in the form of applicator for insertion in the interior of a patient's mouth. In order to facilitate the construction and handling of the apparatus in particular the insertion of the applicator in the mouth, the x-ray apparatus is designed as a unit capable of being positioned on a table or on a wall and contains a stationary member or part, which supports a horizontal axle which pivotably connects a housing containing the x-ray tube and the applicator on the stationary member for pivotable movement therewith. In addition, the installation includes a bite-on part which has a bite piece and a sleeve, which telescopically receives the applicator and enables the patient to locate the applicator in the desired position within the mouth.

10 Claims, 2 Drawing Figures

DENTAL X-RAY DIAGNOSTIC INSTALLATION

BACKGROUND OF THE INVENTION

The present invention is directed to a dental x-ray diagnostic installation which includes an x-ray apparatus containing an x-ray generator, an x-ray tube having a hollow anode forming an applicator which is inserted into the mouth of a patient.

In the case of known dental x-ray diagnostic installations, which have a hollow anode in the form of an applicator which is received in the mouth of the patient, the x-ray apparatus forms a relatively voluminous unit which can be erected on the floor. The unit consists essentially of a column or box in which the x-ray generator and the support mountings for the x-ray tubes are arranged and a chair for the patient, which is rigidly connected to the unit, contains a head support on which the patient's head is fixed or supported in a fixed position.

In order to prepare an x-ray radiograph, the angular position between the row of teeth to be photographed and the x-ray applicator is adjusted. Then the x-ray applicator is inserted into the mouth of the patient by the operating personnel. It is important here to insure that the applicator is arranged on the symetrical axis of the jaw curvature or arch which is being photographed. In the case of this arrangement and handling, the operating personnel can not see into the mouth cavity of the patient so that a danger exists that part of the mouth cavity may be touched by the x-ray applicator during its insertion and as a consequence, the patient can very readily be brought into vomiturition. Thus, the applicator in some instances can cause the patient to gag. Moreover, it is psychologically unfavorable that the patient has no possibility of influencing the process of introduction of the applicator.

SUMMARY OF THE INVENTION

It is the object of the present invention to provide an improved dental x-ray diagnostic installation in particular the object is to construct the installation which is structurally smaller and to provide an installation which enables insertion and alignment of the applicator in the patient's mouth in an easier and more pleasant manner for both the operating personnel as well as for the patient.

To accomplish these objects, the present invention is directed to an improvement of a dental x-ray diagnostic installation which has an x-ray apparatus having an x-ray generator or power source and, an x-ray tube having an applicator receivable orally in a patient's mouth for directing x-rays therefrom. The improvements comprise means for enabling the patient to control the insertion and position of the applicator in the patient's mouth including a mounting structure and a bite-on part. The mounting structure has a support part having means for mounting said support part on a support surface, a housing containing an x-ray tube with the applicator extending from a front surface of the housing and means for pivotably connecting said housing on said support part for pivotable movement on a horizontal axis and including one of said part and housing supporting an axle on a horizontal axis and the other of said part and housing being connected to said axle by bearing mean for enabling rotation on said horizontal axis. The bite-on part includes a bite piece receivable in the patient's mouth and mounted on a guide sleeve, said guide sleeve being telescopically received on said applicator so that the biting of the bite piece by the patient positions the applicator in the desired position in the patient's mouth.

The means for connecting the support part on a support surface enables placing the unit either on a flat table or on a vertical wall. Preferably, the support part contains a flat console containing means for controlling the operation of the x-ray apparatus and has adjustable operating members extending therefrom to enable changing the operating condition of an x-ray such as the exposure intensity and time. The console is designed so that the unit can be either mounted on a table or mounted on a vertical wall. In one embodiment, the means for pivotably connecting includes a vertical support extending from a rear portion of the support part and the housing has a projection extending from a lower surface adjacent a rear surface of the housing which may preferably include the x-ray generator.

In another embodiment the support part is designed for mounting on a vertical wall surface and the means for pivotably connecting includes a support arm extending from the support part and having the axle mounted thereon, said support arm is mounted on the part for movement around a pivot point on the part so that the horizontal axis of the axle can be moved in an arc.

The bite-on part preferably has means provided in the sleeves to limit the depth of insertion of the applicator and the bite-on piece will include a contour such as either depressions or projections to be gripped by the front teeth of the patient. Preferably the means for limiting comprises a closed end on the guide sleeve so that the entire end of the applicator is surrounded by the guide sleeve of the bite-on part.

By utilizing the bite-on part, which can be applied or placed in the mouth of the patient by the patient, it is possible to dispense with a special chair as well as with the additional support elements for the head of the patient. The actual x-ray apparatus can therefore advantageously be designed in a space saving manner which can be either placed on a table or secured on a wall. In particular, the multi-membered unit with costly support arm constructions which were present in the known x-ray installations and required in order to obtain an exact adjustment of the applicator relative to the patient's position in the chair are eliminated.

In the case of the installation of the present invention, the patient can be seated on any chair in front of the x-ray apparatus. The pivot bearings of the connecting means permit the alteration of the angular adjustment of the x-ray tube with the applicator and hence a certain height adjustability. In order to prepare for an x-ray radiograph, the patient himself may insert the bite-on part into his mouth, approach the applicator and as he approaches the applicator can then telescopically insert the x-ray applicator into the sleeve of the bite-on part by himself. Since the x-ray applicator is surrounded and enclosed on all sides by the guide sleeve of the bite-on part, it is not possible for the mechanical irritation of the mouth cavity to occur. The end of the guide sleeve, as mentioned hereinabove, is preferably closed and forms a limit or stop for the depth of penetration for the applicator. Moreover, the bite-on part will exhibit depressions or elevations to create a contour which can be gripped by the patient's teeth and enable cotrolling the depth and insertion of the guide sleeve into the patient's mouth and therefore also the depth of penetration of the x-ray applicator.

DESCRIPTION OF THE PREFERRED EMBODIMENTS

Figure 1:
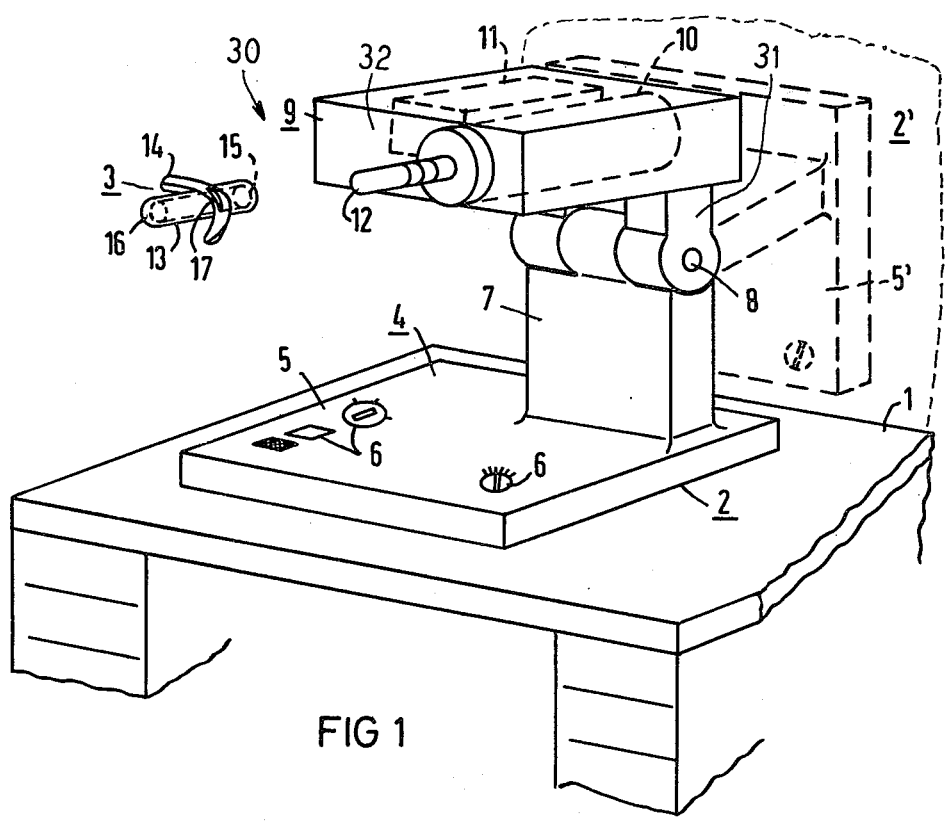
FIG. 1 is a perspective view of an embodiment of a dental x-ray diagnostic installation in accordance with the present invention.

The principles of the present invention are particularly useful in a dental x-ray diagnostic installation generally indicated at 30 in FIG. 1 which includes an x-ray apparatus 2, which is illustrated as being supported on a table 1, and a bite-on part 3.

The x-ray apparatus 2 contains a support part 4, a housing 9 and means for pivotably connecting the housing on the support part 4. As illustrated, the support part 4 includes a flat rectangular housing or console 5, which receives control means for controlling the operation of the x-ray and has control members or knobs 6 extending from a surface therefrom so that the intensity and/or the time of exposure can be selectively changed. At a rear surface of the console 5, a support column or projection 7 extends vertically and on a free end supports a pivot bearing or axle 8 which forms part of the means for pivotably connecting. The housing 9 has a projection 31 which receives the pivot bearing 8 which supports the housing on the part 4. The housing 9, as illustrated, receives an x-ray tube 10, an x-ray generator, which is schematically illustrated by a box 11 and includes the high voltage transformer, and an applicator 12, which extends from the end of the tube 10 and from a front surface 32 of the housing 9. As illustrated, the applicator 12 is a hollow anode from which the x-rays are projected.

The pivot bearing 8 as well as the projection 7 and the projections 31 are designed so that the part 4 and the housing 9 can be adjusted or moved through an angle of at least 90° relative to each other. Thus, if the part 4 is mounted on a wall surface 2' as illustrated in broken lines by the part 5', the housing 9 can still maintain substantially the same position. The part 4 is provided with mounted means which will enable it to be mounted either on a flat horizontal surface such as the table 1 or on a vertical surface such as the wall 2'.

The bite-on part 3 contains a guide sleeve 13 and a bite piece 14 which is arranged on the sleeve 13. Guide sleeve 13 and the bite piece 14 are advantageously fabricated from a sterilizable material. The guide sleeve 13 has a length which corresponds approximately to the length of the applicator 12 and is opened at one end 15 and has an interior diameter slightly larger than the exterior diameter of the applicator 12. Thus, the applicator 12 can be telescopically inserted into the sleeve 13 with a minimum amount of play. The sleeve 13 at an end 16 opposite the opening 15 is closed and forms a limit stop for controlling the depth of insertion of the applicator 12 into the sleeve. The bite piece 14 is shaped to the average jaw shape and is provided with wedge shaped ends. In addition, it is provided with a contour 17, which can be in the form of either elevations or a depression to facilitate gripping or biting by the patient's teeth. The bite-on part 3 can thus be exactly positioned and fixed in the mouth by the patient. A more detailed description of bite-on parts with references to possible variations in their structure is contained in German Gebrauchsmuster No. G 78 20 937.7.

The combination of the bite-on part 13 and the table and/or wall mounted x-ray apparatus 2 makes it possible for the patient to be able to be seated on any type of chair in front of the x-ray apparatus 2. The connecting means including the pivot axle 8 make it possible to alter the angular adjustment of the applicator 12 and hence of the x-ray beam. Through the arrangement of the pivot axle 8 at the rear lower surface of the housing 9, a certain height adjustability can be obtained in order to prepare for an x-ray radiograph. The bite-on part 3 is first received or placed in the patient's mouth. Subsequently, the patient inserts the applicator 12 into the sleeve 13 by approaching the x-ray apparatus and allowing the applicator 12 to be telescopically received in the guide sleeve 13. An irritation of the mouth cavity by the applicator 12 is impossible because the applicator is completely surrounded by the closed guide sleeve 13.

Figure 2:
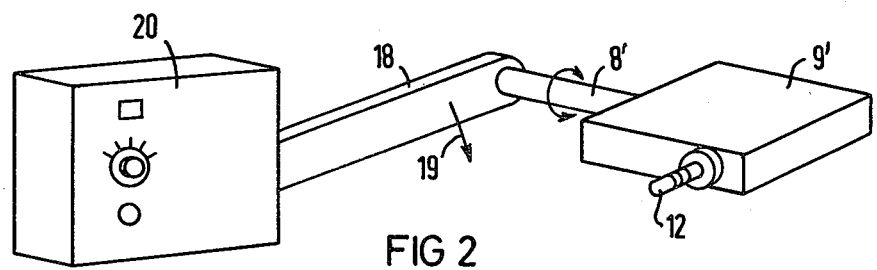
FIG. 2 is a perspective illustration of another embodiment of the present invention.

An embodiment of the installation, which is an embodiment of the x-ray apparatus and is capable of being mounted on a wall, is illustrated in FIG. 2. In the case of this embodiment, the housing 9' has an applicator 12 extending from a front surface. A wall housing or support part 20 has a support arm 18 extending therefrom on which an axle 8' is mounted. The support arm is received in a recess of the part 20 and is pivotably moveable in an arc indicated by the arrow 19. The arm 18 may be of a parallelogram construction so that the arm will move parallel to the surface of the wall. By utilizing a parallelogram, cnstruction for the support arm 18, the arm may be pivoted in the direction of the arrow 19 without rotating or moving the axle 8' so that the housing 9' will have the same angular position relative to a horizontal plane regardless of motion of the arm 18. Thus, once the desired angle for the applicator 12 is achieved, the height of the housing 9' can be changed to accommodate patients of different sizes without changing the angle of the applicator. The housing 9' is also mounted to be pivoted on the axis to enable changing the angle.

A significant advantage of the x-ray diagnostic installation in accordance with the present invention is that the patient can place an auxiliary device such as the bite-on part 3 in his mouth and then insert the applicator 12 without requiring any outside assistance and without contacting the surface of the applicator which contact may trigger gagging or vomiturition. In addition, too great an insertion of the applicator or insertion of the applicator which is otherwise not proper will be eliminated. An additional significant feature is that by means of the bite-on part 3, an exact position of the applicator is obtainable without requiring the necessary positioning measures such as a chair with head supports that are rigidly connected to the x-ray apparatus. Thus, the x-ray apparatus itself can be constructed in a space saving manner to be mounted on a table and/or wall.

Although various minor modifications may be suggested by those versed in the art, it should be understood that we wish to embody within the scope of the patent granted hereon, all such modifications as reasonably and properly come within the scope of our contribution to the art.

We claim:

1. In a dental x-ray diagnostic installation comprising an x-ray apparatus having an x-ray tube having an applicator receivable orally in a patient's mouth for directing x-rays thereform, the improvements comprising means for enabling the patient to control the insertion and position of the applicator in the patient's mouth, said means including a bite-on part and a mounting structure for the x-ray apparatus, said mounting structure having a support part having means for mounting said support part on a support surface, a housing containing said x-ray tube with the applicator extending from a front surface of the housing, and means for pivotably connecting said housing on said support part for pivotable movement on a horizontal axis and including one of said part and housing supporting an axle on a horizontal axis and the other of said part and housing being connected to said axle by bearing means for enabling rotation on said horizontal axis, and said bite-on part including a guide sleeve with a bite piece mounted thereon and being receivable in a patient's mouth, said bite piece having a shape of an average jaw shape with a contour for receiving the front teeth of the patient, said guide sleeve having an opening with an interior diameter slightly larger than an exterior diameter of the applicator and being telescopically received on said applicator so that the biting of the bite piece by the patient positions the bite-on part in the desired position as the applicator is telescopically inserted in the guide sleeve.

2. In a dental x-ray diagnostic installation according to claim 1, wherein a high voltage source for the x-ray tube is disposed in said housing.

3. In a dental x-ray diagnostic installation according to claim 2, wherein the means for pivotably connecting includes the housing having a projection extending from a lower surface adjacent a rear surface of said housing.

4. In a dental x-ray diagnostic installation according to claim 1, wherein the support part contains a flat console containing means for controlling the operation of the x-ray apparatus, said console having adjustment and operating members arranged thereon, and wherein the means for pivotably connecting includes a vertical support extending from a rear portion of said support part.

5. In a dental x-ray diagnostic installation according to claim 4, wherein said means for mounting the support part can mount the support part on both vertical and horizontal surfaces so that said console is designed for the purpose of enabling operation of the device with the support part being mounted on both horizontal and vertical surfaces.

6. In a dental x-ray diagnostic installation according to claim 1, wherein the means for mounting the support part mounts the support part on a vertical surface, said means for pivotably connecting including a support arm extending from said support part having the axle mounted thereon, said support arm being mounted on said part for movement around a pivot point on said part so that the horizontal axis of said axle can be moved in an arc.

7. In a dental x-ray diagnostic installation according to claim 6, wherein said arm includes means for maintaining the axle and housing in a fixed angular relation as the arm pivots on the part.

8. In a dental x-ray diagnostic installation according to claim 1, wherein the guide sleeve of the bite-on part has means for limiting the depth of insertion of the applicator therein.

9. In a dental x-ray diagnostic installation according to claim 8, wherein said means for limiting comprises a close end of said guide sleeve of the bite-on part.

10. A method of positioning an applicator of an x-ray tube of an x-ray apparatus in the mouth of a patient, said method comprising the steps of providing an x-ray diagnostic installation having a mounting structure comprising a housing containing an x-ray tube with an applicator extending from a front surface of the housing, a support part having means for mounting said support part on a support surface and means for pivotally connecting said housing on said support part for pivotal movement on a horizontal axis including one of said part and housing supporting an axle on the horizontal axis and the other of said part and housing being connected to said axle by bearing means to enable rotation on the horizontal axis; providing a bite-on part including a guide sleeve with a bite piece mounted thereon and receivable in the patient's mouth, said bite piece having a shape of an average jaw shape with a contour for receiving the front teeth of the patient, said guide sleeve having an opening with an interior diameter slightly larger than an extension diameter of the applicator and being telescopically receivable on said applicator; then positioning the bite-on part in the patient's mouth by having the patient's front teeth grip the contour of the bite piece; inserting the applicator into the guide sleeve and adjusting the housing on said horizontal axis while inserting the applicator to enable movement of the applicator into said guide sleeve with a minimum amount of play so that the applicator of the x-ray tube is positioned in the desired position in the patient's mouth without gagging the patient.

* * * * *